(12) United States Patent
Baeuerle et al.

(10) Patent No.: US 11,169,133 B2
(45) Date of Patent: Nov. 9, 2021

(54) MEASURING DEVICE FOR PROCESS METROLOGY

(71) Applicant: Berthold Technologies GmbH & Co. KG, Bad Wildbad (DE)

(72) Inventors: Joerg Baeuerle, Baiersbronn (DE); Steffen Mueller, Pforzheim (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 0 days.

(21) Appl. No.: 16/945,109

(22) Filed: Jul. 31, 2020

(65) Prior Publication Data

US 2021/0041413 A1    Feb. 11, 2021

(30) Foreign Application Priority Data

Aug. 9, 2019  (DE) .................... 10 2019 212 018.0

(51) Int. Cl.
*G01N 33/20*        (2019.01)
(52) U.S. Cl.
CPC .................................... *G01N 33/20* (2013.01)
(58) Field of Classification Search
CPC combination set(s) only.
See application file for complete search history.

(56) References Cited

U.S. PATENT DOCUMENTS

2018/0328767 A1   11/2018   Adachi et al.
2020/0145513 A1    5/2020   Verma et al.

FOREIGN PATENT DOCUMENTS

DE    11 2018 001 589 T5    12/2019

OTHER PUBLICATIONS

German-language Search Report issued in German Application No. 10 2019 212 018.0 dated Mar. 24, 2020 with partial English translation (five (5) pages).

*Primary Examiner* — Janet L Suglo
(74) *Attorney, Agent, or Firm* — Crowell & Moring LLP

(57) ABSTRACT

A measuring device includes: a number n of sensors, a respective sensor of the number n of sensors being embodied to generate associated sensor data such that, overall, a number n of sensor data is generated by the number n of sensors; a learning unit embodied to calculate values of a number d of parameters of a hypothesis function on the basis of training data; a first measured quantity calculation unit to calculate a number m of first measured quantity values depending on the number n of sensor data on the basis of the hypothesis function and the calculated values of the number d of parameters of the hypothesis function; a second measured quantity calculation unit to calculate a number m' of second measured quantity values depending on the number n of sensor data on the basis of a model function; and a status unit which checks the calculation of the first measured quantity values on the basis of the second measured quantity values.

11 Claims, 2 Drawing Sheets

MEASURING DEVICE FOR PROCESS METROLOGY

CROSS REFERENCE TO RELATED APPLICATION

This application claims priority under 35 U.S.C. § 119 from German Patent Application No. 10 2019 212 018.0, filed Aug. 9, 2019, the entire disclosure of which is herein expressly incorporated by reference.

BACKGROUND AND SUMMARY OF THE INVENTION

The invention relates to a measuring device for process metrology.

In process metrology, radiometric and/or microwave-based measuring devices, which comprise radiometric sensors for radiation measurement and/or microwave sensors, are frequently used for the purposes of measuring process variables or material properties, for example for the purposes of measuring fill level, for measuring density, etc.

The invention is based on the object of providing a measuring device which facilitates a reliable determination of values of a number of quantities to be measured, even in the case of complex radiometric measurement problems and/or microwave-based measurement problems.

The invention achieves this object by a measuring device for use in process metrology, according to the independent claim.

The measuring device has a number n of sensors, where n is a natural number greater than zero. By way of example, the number n can range between one and 12.

A respective sensor of the number n of sensors is embodied to generate its associated sensor data such that, overall, a number n of sensor data is generated by means of the number n of sensors. By way of example, the sensor data are each data in digital representation, for example with a resolution between 8 bit and 64 bit. The digital sensor data are generated, e.g., continuously with a specified temporal repetition rate. By way of example, the data of all n sensors are generated simultaneously or with a known temporal relationship with respect to one another every 100 ms.

The measuring device further has a learning unit, the learning unit being embodied to calculate values of a number d of parameters of a hypothesis function on the basis of training data.

The measuring device further has a first measured quantity calculation unit which is embodied to calculate a number m of first measured quantity values depending on the number n of sensor data on the basis of the hypothesis function and the previously calculated values of the number d of parameters of the hypothesis function. In particular, the hypothesis function h approximates a measurement function f. The sensor data can also be time offset. The number m is a natural number greater than zero and, for example, can range between one and 4. The number d is a natural number greater than zero and, for example, can range between one and 500. The measured quantity values represent, for example, a corresponding number of process variables to be measured.

The measuring device further has a second measured quantity calculation unit which is embodied to calculate a number m' of second measured quantity values depending on the number n of sensor data on the basis of a model function g. The numbers m and m' can be identical or different. Typically, m≥m' applies.

The measuring device further has a status unit which checks the calculation of the first measured quantity values on the basis of the second measured quantity values.

The learning unit, the number of sensors, the first and second measured quantity calculation unit and the status unit can be provided spatially together or spatially separated from one another. By way of example, the number of sensors, the first and second measured quantity calculation unit and the status unit can be disposed at the location of the measurement problem, i.e., in the field, and the learning unit can be disposed spatially separately therefrom. By way of example, the learning unit can be realized by means of a powerful computer which calculates the number d of parameters on the basis of the training data, with the number d of parameters subsequently being made available to the first measured quantity calculation unit, for example by virtue of the number d of parameters being transmitted from the learning unit to the first measured quantity calculation unit via a data network. Naturally, the learning unit and the first and the second measured quantity calculation unit, and optionally the number n of sensors as well, can be integrated in a common physical device.

According to one embodiment, the number m of first measured quantity values is selected from the set of measured quantity values consisting of: measured quantity values of a fill level, measured quantity values of positions and/or thicknesses of individual material layers, measured quantity values of a density, measured quantity values of a conveying capacity, in particular an overall conveyed mass, measured quantity values of a throughput, in particular of a mass flow, measured quantity values of a moisture, measured quantity values of a content of solid matter, measured quantity values of a sugar content, measured quantity values of a concentration and a material composition, in particular of chemical compositions.

According to one embodiment, the number n of sensors is selected from the set of sensors consisting of: at least one radiometric sensor, in particular a radiometric sensor which is embodied to generate sensor data in the form of a count rate or radiation intensity data and/or a radiometric sensor which is embodied to generate sensor data in the form of information about radiometric spectra, at least one sensor which is embodied to generate sensor data in the form of temperature data, at least one sensor which is embodied to generate sensor data in the form of acceleration data, at least one sensor which is embodied to generate sensor data in the form of speed data, at least one sensor which is embodied to generate sensor data in the form of position data, at least one sensor, in particular in the form of an ultrasonic sensor or laser sensor, which is embodied to generate sensor data in the form of information about a load height profile, at least one sensor which is embodied to generate sensor data in the form of moisture data, at least one microwave sensor, at least one sensor which is embodied to generate sensor data in the form of conductivity data, and at least one sensor which is embodied to generate sensor data in the form of pressure data.

In the case of complex measurement problems, the relationships between sensor data and measured quantity values are not always exactly describable in analytic fashion. Therefore, this relationship previously had to be approximated using suitable physical and mathematical models. However, the measurement model is often unknown or approximated too simplistically, no suitable model for sensor fusion is known and/or the measurement model is too complicated. Therefore, overall, the quality of the measured quantity values or process values calculated in the measuring system suffers.

According to the invention, this problem is solved by virtue of the measuring device establishing relationships between sensor data and measured quantity values by using processes from artificial intelligence (AI), such as "machine learning" or "deep learning" in an automated, self-learning fashion on the basis of training data and without explicit knowledge of an analytic measurement equation.

This increases the measurement accuracy by reducing systematic errors. The quality and accuracy of the calculated measured quantity values are increased since the measuring device learns the totality of all process influences with the aid of the training data. In addition to the known influences, these contain also unknown disturbance influences, in particular, the existence of which is not yet known during commissioning, for example. Therefore, the measuring device may even contain more expert knowledge than a human operator and process expert in the field. This leads to significant improvement in the measured quantity value accuracy.

Further, previously unsolvable measurement tasks become solvable. In contrast to conventional measuring systems in process metrology, the invention requires no explicit measurement model to be known in advance. Rather, the measuring device creates the measurement model itself by means of artificial intelligence. Consequently, the physical process to be measured can be treated as a black box, the internal logic of which is unknown, and learned and organized by the measuring device itself. As a result, the invention also provides for measurement problems for novel, previously alien or unsolvable physical processes to be solved. This offers a significant advantage since new markets and problems can be opened up without expert knowledge or with only rudimentary specialist knowledge in the respective domain. The measuring device according to the invention acquires the expert knowledge itself.

Further, the measuring device according to the invention has lower memory requirements in comparison with conventional solutions with similar capabilities. If the amount of information processed and learned during the learning phase according to the invention is compared to the number of model parameters, the memory requirements of the measuring device according to the invention are comparatively modest. If the intention were to obtain similar measurement powers using conventional measuring devices (to the extent that this is even possible), comprehensive calibration tables would be necessary, said calibration tables exceeding all memory limits of embedded systems.

Further, the measuring device according to the invention facilitates shorter cycle times and higher update rates. The calculation steps for processing the sensor data into the measured quantity values during the measurement process, performed by the measuring device according to the invention, are largely based on processes from linear algebra, specifically on matrix-vector multiplications. On appropriate hardware, these operations are carried out in significantly more performant fashion than conventional procedural mathematical algorithms from process metrology. This leads to shorter cycle times of the measuring system and consequently to higher update rates in the process control system on the customer side.

Further, the measuring device according to the invention facilitates shorter design times. Since only little expert knowledge from the respective specialist domain is necessary according to the invention, individual customer solutions for novel measurement problems can be worked out more quickly. The associated measuring systems can be designed and individualized in significantly simpler fashion. This saves time and reduces costs.

Further, the measuring device according to the invention facilitates a simpler operation. Calibrating the measuring device according to the invention is very simple. Instead of determining complex, measurement application-specific calibration parameters like in the case of conventional measuring devices, only training data have to be recorded according to the invention. Then, the measuring device calibrates itself by means of the learning unit. For the user, this unifies the calibration process in measurement application-overarching fashion and makes it significantly simpler.

However, since the AI-ascertained measurement model is not available in hard-encoded fashion or set a priori, it is not possible to formally prove that such a measuring system always supplies the correct measured quantity values in every situation and for any combination of input values. This represents a problem, in particular for safety-critical applications in process metrology, in particular in view of software and device approval.

According to the invention, the solution to this problem is achieved by virtue of the AI measuring system—in particular in the form of the first measured quantity calculation unit in conjunction with the learning unit—being combined with a second measured quantity calculation unit, the second measured quantity calculation unit being based on a simplified mathematical-analytical measurement model, which is represented by the model function g. By means of the second measured quantity calculation unit, it is now possible to check the plausibility or monitor the measured quantity values calculated by means of the first measured quantity calculation unit.

The invention facilitates an improvement in the robustness and predictability of measured quantity values calculated by artificial intelligence in safety-critical applications in radiometric and microwave-technical process metrology.

The measuring device according to the invention is more robust in relation to interference conditions and marginal cases. By way of example, marginal cases which possibly falsify an AI-based calculation of the first measured quantity values are detected and the falsified first measured quantity values are possibly even suitably corrected. Thus, the measuring device according to the invention unifies the AI-based measured quantity value accuracy and the robustness of the mathematical-analytical measured quantity value calculation.

Compared to purely AI-based measuring devices, the measuring device according to the invention behaves more deterministically since the calculation of the first measured quantity values is forced into a known but dynamic tolerance corridor about the second measured quantity values calculated on the basis of a mathematical-analytical model. Since the mathematical-analytical calculation can be present in hard-encoded fashion, it is possible to formally prove how this measured quantity value tolerance corridor is set up. This substantially increases the admissibility of the measuring device, and so the measuring device according to the invention makes the use of AI processes significantly safer for safety-critical applications in radiometric and microwave-technical process metrology.

According to one embodiment, the model function is determined during a calibration procedure for the measuring device.

According to one embodiment, the model function is determined by means of a linear regression and/or nonlinear parameter fitting.

According to one embodiment, the measuring device has a fusion unit which is embodied to calculate a number m of fusion measured quantity values depending on the first measured quantity values and the second measured quantity values.

According to one embodiment, the status unit is embodied to generate an alarm if the first measured quantity values deviate too strongly from the second measured quantity values according to specified criteria.

According to one embodiment, the fusion unit has a Kalman filter which fuses the first measured quantity values and the second measured quantity values to calculate the number m of fusion measured quantity values.

According to one embodiment, the fusion unit has a particle filter which fuses the first measured quantity values and the second measured quantity values to calculate the number m of fusion measured quantity values.

According to one embodiment, the fusion unit is embodied to form a weighted mean of the first measured quantity values and the second measured quantity values to calculate the number m of fusion measured quantity values.

According to one embodiment, the learning unit is embodied to extract training sensor data from the training data and to extract associated setpoint values of the number m of first measured quantity values, the measured quantity calculation unit being embodied to calculate training values of the number m of first measured quantity values depending on the training sensor data and the learning unit being embodied to calculate the values of the number d of parameters on the basis of the setpoint values of the number m of first measured quantity values and the training values of the number m of first measured quantity values.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
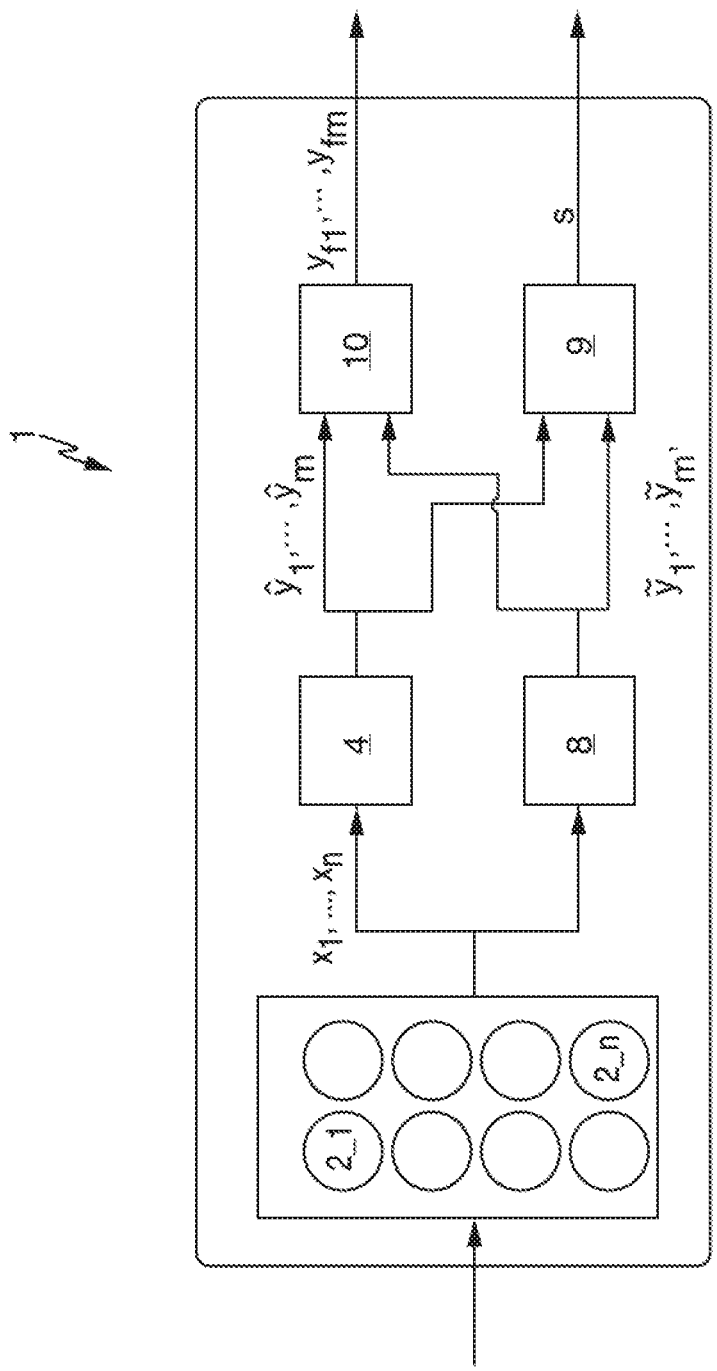
FIG. 1 very schematically shows a block diagram of a measuring device according to an embodiment of the invention.

FIG. 1 very schematically shows a block diagram of a measuring device 1.

The measuring device 1 has a number n of sensors 2_1 to 2_n, a respective sensor 2_i of the number n of sensors 2_1 to 2_n being embodied to generate associated sensor data $x_i$ such that, overall, a number n of sensor data $x_1, \ldots, x_n$, is generated by means of the number n of sensors 2_1 to 2_n.

Further, the measuring device 1 has a first measured quantity calculation unit 4 which is embodied to calculate a number m of first measured quantity values $\hat{y}_1, \ldots, \hat{y}_m$ depending on the number n of sensor data $x_1, \ldots, x_n$, on the basis of values of a number d of parameters $\theta_1, \ldots, \theta_d$ of a hypothesis function $h_\theta$.

Figure 2:
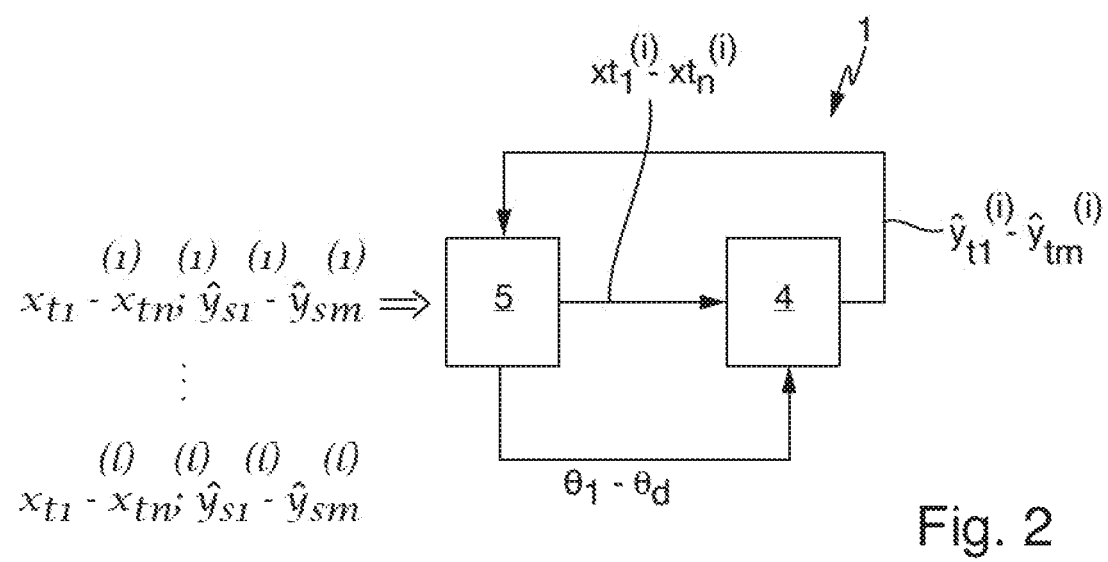
FIG. 2 very schematically shows a block diagram of the measuring device shown in FIG. 1 in a learning mode of operation.

With reference to FIG. 2, the measuring device 1 has a learning unit 5, the learning unit 5 being embodied to calculate the values of the number d of parameters $\theta_1, \ldots, \theta_d$ on the basis of training data $xt_i^{(i)}, \ldots, xt_n^{(i)}$; $\hat{y}s_1^{(i)}, \ldots, \hat{y}s_m^{(i)}$.

The measuring device 1 converts input quantities in the form of the sensor data $x_1, \ldots, x_n$, which may also be time offset, into output quantities in the form of the process measured quantities or first measured quantity values $\hat{y}_1, \ldots, \hat{y}_m$.

The conversion depends on the model parameters $\theta_1, \ldots, \theta_d$, which are initially unknown and which are learned by means of the learning unit 5 by means of so-called machine learning. In the process, recorded training data, also referred to as learning data, are used; these may be formed from real recorded data during the operation and/or from simulation data.

Machine learning means that the measuring device generates artificial knowledge from experience. The measuring device learns from examples and can generalize these once the learning phase has been completed. This means that the examples are not simply learned by rote; instead, the measuring device identifies patterns and laws in the training data. Thus, it is also possible to assess unknown data (learning transfer).

The measuring device preferably uses learning techniques from so-called supervised learning, in which the measuring device learns a measurement function from given pairs of inputs and outputs. Here, the correct measured quantity values for a number n of sensor data are provided in the learning, for example on the basis of a reference measurement or a simulation.

Thus, the measuring device formally approximates a measurement function $f:(x_1, \ldots, x_n) \mapsto (y_1, \ldots, y_m)$, which maps n input variables or sensor data $x_1, \ldots, x_n$ onto m output variables or first measured quantity values $y_1, \ldots, y_m$ by way of a suitable hypothesis function $h_\theta: (x_1, \ldots, x_n) \mapsto (\hat{y}_1, \ldots, \hat{y}_m)$ which maps the n sensor data $x_1, \ldots, x_n$ onto m estimated values $\hat{y}_1, \ldots, \hat{y}_m$ for the $y_1, \ldots, y_m$ and which is dependent on the model parameters $\theta:=(\eta_1, \ldots, \theta_d)$.

Here, each of the d individual model parameters $\theta_i$ is understood to be one of the following three things:

a mathematical object, in particular
a number,
a vector,
a function,
a parameterized piece of program logic or source code,
a piece of program logic or source code generated by a code generator.

The model parameters $\theta_1, \ldots, \theta_d$ are learned by the learning algorithm from training data. More precisely, training data consist of l (where l ranges between $10^5$ and $10^7$, for example, in particular where $l=10^6$ applies) training pairs $(xt^{(1)}, \hat{y}s^{(1)}), \ldots, (xt^{(l)}, \hat{y}s^{(l)})$ which, e.g., each have a dimension of n+m and, for example, consist of a complete set of input data or training sensor data $xt^{(i)}:=(xt_1^{(i)}, \ldots, xt_n^{(i)})$ plus associated setpoint values $\hat{y}s^{(i)}=(\hat{y}s_1^{(i)}, \ldots, \hat{y}s_m^{(i)})$ of the number m of first measured quantity values, where $i=1, \ldots, l$. The setpoint values $\hat{y}s_1^{(i)}, \ldots, \hat{y}s_m^{(i)}$ are also referred to as training labels.

On the basis of the training sensor data $xt_1^{(i)}, \ldots, xt_n^{(i)}$, the measured quantity calculation unit 4 calculates the training values $(\hat{y}t_1^{(i)}, \ldots, \hat{y}t_m^{(i)}):=h_\theta(xt_i^{(i)}, \ldots, xt_n^{(i)})$ of the number m of first measured quantity values $\hat{y}_1, \ldots, \hat{y}_m$, which are dependent on the parameters $\theta_1, \ldots, \theta_d$. For $i=1, \ldots, l$, the learning unit 5 is embodied to calculate the values of the parameters $\theta_1, \ldots, \theta_d$ on the basis of the setpoint values $\hat{y}s_1^{(i)}, \ldots, \hat{y}s_m^{(i)}$ and the training values $\hat{y}t_1^{(i)}, \ldots, \hat{y}t_m^{(i)}$.

The calculation of the model parameters $\theta_1, \ldots, \theta_d$ can be carried out iteratively a number of times. That is to say, random start parameters $\theta_1, \ldots, \theta_d$ are initially used. These are then improved iteratively by virtue of all $\hat{y}t_1^{(i)}, \ldots, \hat{y}t_m^{(i)}$ being calculated repeatedly on the basis of the respectively current $\theta_1, \ldots, \theta_d$ and then new, improved $\theta_1, \ldots, \theta_d$ therefrom, until a specifiable quality measure is reached (e.g., a minimum of a cost function). Additionally, only a subset of the total of l data records $\hat{y}t_1^{(i)}, \ldots, \hat{y}t_m^{(i)}$, a so-called mini batch, can be used in each iteration step in order to calculate new $(\theta_1, \ldots, \theta_d)$. That is to say, a plurality of iterations may be necessary in order to once take account of the entire training data, a so-called training epoch.

The learning algorithm is performed, e.g., once when initiating the measuring device or repeatedly in real time during the operation of the measuring device, e.g., by way of additional reference measurements.

The measuring device 1 further has a second measured quantity calculation unit 8 which is embodied to calculate a number m' of second measured quantity values $\tilde{y}_1, \ldots, \tilde{y}_{m'}$ depending on the number n of sensor data $x_1, \ldots, x_n$, on the basis of a mathematical-analytical model function g.

The measuring device 1 further has a status unit 9 which checks the calculation of the first measured quantity values $\hat{y}_1, \ldots, \hat{y}_m$ on the basis of the second measured quantity values $\tilde{y}_1, \ldots, \tilde{y}_{m'}$ for example by virtue of the first measured quantity values $\hat{y}_1, \ldots, \hat{y}_m$, calculated by means of AI, being compared to the second measured quantity values $\tilde{y}_1, \ldots, \tilde{y}_{m'}$.

Should the first measured quantity values $\hat{y}_1, \ldots, \hat{y}_m$ be classified as valid, the status unit 9 can fuse the first measured quantity values $\hat{y}_1, \ldots, \hat{y}_m$ with the second measured quantity values $\tilde{y}_1, \ldots, \tilde{y}_{m'}$ by means of sensor fusion (e.g., Kalman filter, particle filter or weighted mean value) to form more robust measured quantity values.

According to the invention, the measurement function $f:(x_1, \ldots, x_n) \mapsto (y_1, \ldots, y_m)$ still is additionally approximated by the model function $g:(x_1, \ldots, x_n) \mapsto (\tilde{y}_1, \ldots, \tilde{y}_{m'})$.

which maps the n sensor data $x_1, \ldots, x_i$, on the m' second measured quantity values $\tilde{y}_1, \ldots, \tilde{y}_{m'}$ as approximate values for $y_1, \ldots, y_m$.

The second measured quantity values $\tilde{y}_1, \ldots, \tilde{y}_{m'}$ are based on a mathematical-analytical measurement model.

By way of example, the model function g is determined during the calibration process, for example by means of linear regression or nonlinear parameter fitting. As a rule, g will be a significantly simpler model than $h_\theta$ and the second measured quantity values $\tilde{y}_1, \ldots, \tilde{y}_m$ will consequently have a significantly lower accuracy than the first measured quantity values $\hat{y}_1, \ldots, \hat{y}_m$; however, they typically are more robust and predictable.

According to the invention, provision can be made of a status function S $S:((\hat{y}_1, \ldots, \hat{y}_m), \tilde{y}_1, \ldots, \tilde{y}_{m'})) \mapsto s$, which maps the first measured quantity values $\hat{y}_1, \ldots, \hat{y}_m$ and the second measured quantity values $\tilde{y}_1, \ldots, \tilde{y}_{m'}$ onto a status s, which serves as a quality or error measure for the first measured quantity values $\hat{y}_1, \ldots, \hat{y}_m$. By way of example, the status s is used to trigger an alarm as soon as the first measured quantity values $\hat{y}_1, \ldots, \hat{y}_m$ and the second measured quantity values $\tilde{y}_1, \ldots, \tilde{y}_m$ deviate too strongly from one another according to certain, suitable criteria. The status s can be a number or a vector of any dimension. In particular, it is possible that $s=(s_1, \ldots, s_m)$, where each partial status $s_i$ is an individual quality or error measure for the associated $\hat{y}_i$. In particular, metrics, similarity functions, thresholds and/or statistical models can be used in S in order to calculate s.

In one possible embodiment, for example, the assumption is made that the difference vector $\delta := (\delta_1, \ldots, \delta_m) := (\hat{y}_1, \ldots, \hat{y}_m) - (\tilde{y}_1, \ldots, \tilde{y}_m)$ between the first measured quantity values $\hat{y}_1, \ldots, \hat{y}_m$ and the second measured quantity values $\tilde{y}_1, \ldots, \tilde{y}_{m'}$ has a multivariate normal distribution. During the training phase of the AI-based measured quantity ascertainment, the mean value vector $\mu_\delta$ and the sample covariance matrix $\Sigma_\delta$ are then determined and the m-dimensional normal distribution $\delta \sim \mathcal{N}(\mu_\delta, \Sigma_\delta)$ is adapted to the training output values. During measurement operation, the status function S then calculates the status value s depending on the value of the probability density of the current difference vector $\delta$. By way of example, S can be defined as $S((\hat{y}_1, \ldots, \hat{y}_m), (\tilde{y}_1, \ldots, \tilde{y}_m)) := 1 - \exp(-\alpha \cdot (\delta - \mu_\delta)^T \Sigma_D^{-1}(\delta - \mu_\delta))$ and can be interpreted as a continuous alarm level, which moves between 0 and 1 and which is always close to 1 when the first measured quantity values $\hat{y}_1, \ldots, \hat{y}_m$ and the second measured quantity values $\tilde{y}_1, \ldots, \tilde{y}_{m'}$ deviate too strongly from one another.

The free design parameter $\alpha > 0$ facilitates the fine-tuning of the desired level increase.

In addition to the status function S, the solution according to the invention optionally comprises a fusion function F $F:((\hat{y}_1, \ldots, \hat{y}_m), (\tilde{y}_1, \ldots, \tilde{y}_m)) \mapsto (z_1, \ldots, z_m)$ which maps the first measured quantity values $\hat{y}_1, \ldots, \hat{y}_m$ and the second measured quantity values $\tilde{y}_1, \ldots, \tilde{y}_{m'}$ onto more robust measured quantity values $z_1, \ldots, z_m$. In particular, Kalman filters, particle filters or weighted mean values can be used in F and the $z_1, \ldots, z_m$ can be restricted to certain valid value ranges (capping).

By way of example, the measuring device 1 can facilitate a multi-phase meniscus measurement (steel plus powder).

By way of example, the sensors 2_1 to 2_n can form n scintillator modules as mutually independent count rate detectors, where n can equal 10, for example. Two fill levels $(y_1, y_2)$ are calculated as measured quantity values (steel fill level and casting powder height), i.e., m=2.

An artificial neural network can be used as an AI model, the weights of which are learned as model parameters $\theta$ by means of back propagation from training data (e.g., field data or simulation data). The AI hypothesis function $h_\theta$ pushes the individual count rates $x_1, \ldots, x_n$ of the individual scintillator modules 2_1 to 2_n through the neural network during measurement operation and maps these onto the output values $(\hat{y}_1, \hat{y}_2)$ thereof.

Consequently, $h_\theta$ supplies both an accurate steel fill level and an accurate casting powder height but, as a black box, it is potentially susceptible to statistical outliers and marginal cases, which have not been considered exhaustively in the training and test phase.

By contrast, the model function g calculates the sum $\Sigma_{i=1}^n x_i$ over the count rates of all scintillator modules and maps this summed count rate to a steel fill level $\tilde{y}_1$ via a conventional calibration table by means of linear interpolation. The casting powder height $\tilde{y}_2$, which is determined by g, is constantly 0.

Consequently, g supplies a predictable, approximate but robust steel fill level, but no information about the casting powder height.

The status function S is defined as $$S((\hat{y}_1, \hat{y}_2), (\tilde{y}_1, \tilde{y}_2)) := 1 - \exp\left(-a \cdot \frac{(\hat{y}_1 - \tilde{y}_1 - \mu_{\delta_1})^2}{\sigma_{\delta_1}^2}\right) \quad 5$$

i.e., the functional value of S is an alarm level which moves continuously between 0 and 1 and which is close to 1 when the AI hypothesis function $h_\theta$ supplies an outlier for the steel fill level $\hat{y}_1$ which significantly contradicts the conventional steel fill level $\tilde{y}_1$ of g. The powder height $\hat{y}_2$ is not evaluated here, since g makes no real statement about the casting powder height. The distribution parameters $\mu_{\delta_1}$ and $\sigma_{\delta_1}$ for the steel fill level difference are calculated during the training phase of the AI and, for example, $\alpha=0.08$ is chosen in order to model a desired level increase.

The fusion function F is defined as $$F((\hat{y}_1, \hat{y}_2), (\tilde{y}_1, \tilde{y}_2)) := \begin{pmatrix} \alpha_1 \cdot \hat{y}_1 + (1 - \alpha_1) \cdot \tilde{y}_1 \\ \alpha_2 \cdot \hat{y}_2 + (1 - \alpha_2) \cdot \tilde{y}_2 \end{pmatrix}$$

i.e., the first measured quantity values $\hat{y}_1, \hat{y}_2$ are provided with the weights $\alpha_1$ and $a_2$ in this case and combined with the second measured quantity values $\tilde{y}_1, \tilde{y}_2$ by calculation, e.g., with $\alpha_1=0.85$ for the steel fill level and $\alpha_2=1.0$ for the casting powder height.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A measuring device for process metrology, comprising:
    a number of n sensors ($2_1$ to $2n$), a respective sensor ($2_i$) of the number of n sensors being embodied to generate associated sensor data ($x_i$) such that a number of n sensor data ($x_1, \ldots, x_n$) is generated by way of the number of n sensors wherein
    the number of n snesors is selected from a group of sensors comprising at least one of:
        a radiometric sensor which is embodied to generate sensor data in the form of a count rate or radiation intensity data,
        a radiometric sensor which is embodied to generate sensor data in the form of information about radiometric spectra,
        an ultrasonic sensor or laser sensor, which is embodied to generate sensor data in the form of information about a load height profile, or
        a microwave sensor;
    a computer to learn, using a learning algorithm, values of a number d of parameters ($\theta_1, \ldots, \theta_d$) of a hypothesis function ($h_\theta$) based on training pairs (($xt_1^{(i)}, \ldots, xt_n^{(i)}$);($\hat{y}s_1^{(i)}, \ldots, \hat{y}s_m^{(i)}$));
    a processor communicatively coupled to the number of n sensors and
    a memory in communication with the processor, the memory storing a plurality of instructions executable by the processor to cause the measuring device to,
    convert the number of n sensor data ($x_1, \ldots, x_n$) to a number m first measured quantity values ($\hat{y}_1, \ldots, \hat{y}_m$) via the hypothesis function ($h_\theta$), depending on the learned number d of parameters ($\theta_1, \ldots, \theta_d$);
    convert the number of n sensor data ($x_1, \ldots, x_n$) to a number m' of second measured quantity values ($\tilde{y}_1, \ldots, \tilde{y}_{m'}$) depending via a mathematical-analytical measurement model function (g) determined using a linear regression or a nonlinear parameter fitting;
    determine the validity of the first measured quantity values ($\hat{y}_1, \ldots, \hat{y}_m$) on the basis of the second measured quantity values ($\tilde{y}_1, \ldots, \tilde{y}_{m'}$); and
    fuse the first measured quantity values ($\hat{y}_1, \ldots, \hat{y}_m$) and the second measured quantity values ($\tilde{y}_1, \ldots, \tilde{y}_{m'}$) into a number m of fusion measured quantity values ($yf_1, \ldots, yf_m$).

2. The measuring device according to claim 1, wherein the number m of first measured quantity values (($\hat{y}_1, \ldots, \hat{y}_m$) is selected from a group of measured quantity values comprising:
    measured quantity values of a fill level,
    measured quantity values of positions and/or thicknesses of individual material layers,
    measured quantity values of a density,
    measured quantity values of a conveying capacity, including an overall conveyed mass,
    measured quantity values of a throughput, including a mass flow,
    measured quantity values of a moisture,
    measured quantity values of a content of solid matter,
    measured quantity values of a sugar content,
    measured quantity values of a concentration, or
    a material composition, including chemical compositions.

3. The measuring device according to claim 1, wherein the number of n sensors is selected from a group of sensors further comprising:
    at least one sensor which is embodied to generate sensor data in the form of temperature data,
    at least one sensor which is embodied to generate sensor data in the form of acceleration data,
    at least one sensor which is embodied to generate sensor data in the form of speed data,
    at least one sensor which is embodied to generate sensor data in the form of position data,
    at least one sensor which is embodied to generate sensor data in the form of moisture data,
    at least one sensor which is embodied to generate sensor data in the form of conductivity data, or
    at least one sensor which is embodied to generate sensor data in the form of pressure data.

4. The measuring device according to claim 1, wherein the model function (g) is determined during a calibration procedure for the measuring device.

5. The measuring device according to claim 1, wherein the memory further comprises instructions executable by the processor to cause the measuring device to:
    generate an alarm if the first measured quantity values ($\hat{y}_1, \ldots, \hat{y}_m$) deviate from the second measured quantity values ($\tilde{y}_1, \ldots, \tilde{y}_{m'}$) according to specified criteria.

6. The measuring device according to claim 1, further comprising:
    a Kalman filter to fuse the first measured quantity values ($\hat{y}_1, \ldots, \hat{y}_m$) and the second measured quantity values ($\tilde{y}_1, \ldots, \tilde{y}_{m'}$) into the number m of fusion measured quantity values ($yf_1, \ldots yf_m$).

7. The measuring device according to claim 1, further comprising:

a particle filter to fuse the first measured quantity values ($\hat{y}_1, \ldots, \hat{y}_m$) and the second measured quantity values ($\tilde{y}_1, \ldots, \tilde{y}_{m'}$) into the number of m of fusion measured quantity values ($yf_1, \ldots, yf_m$).

8. The measuring device according to claim 1, wherein the memory further comprises instructions executable by the processor to cause the measuring device to:
   form a weighted mean of the first measured quantity values ($\hat{y}_1, \ldots, \hat{y}_m$) and the second measured quantity values ($\tilde{y}_1, \ldots, \tilde{y}_{m'}$) into the number m of fusion measured quantity values ($yf_1, \ldots, yf_m$).

9. The measuring device according to claim 1, wherein the computer is further configured to:
   extract a number of n training sensor data ($xt_1^{(i)}, \ldots, xt_n^{(i)}$) from the training data (($xt_1^{(i)}, \ldots, xt_n^{(i)}$); ($\hat{y}s_1^{(i)}, \ldots, \hat{y}s_m^{(i)}$)), and
   extract a number m of associated setpoint values ($\hat{y}s_1^{(i)}, \ldots, \hat{y}s_m^{(i)}$) of the number m of first measured quantity values ($\hat{y}_1, \ldots, \hat{y}_m$);
   the memory further comprises instructions executable by the processor to cause the measuring device to:
     generate a number m of training values ($\hat{y}t_1^{(i)}, \ldots, \hat{y}t_m^{(i)}$) of the number m of first measured quantity values ($\hat{y}_1, \ldots, \hat{y}_m$) depending on the number of n training sensor data ($xt_1^{(i)}, \ldots, xt_n^{(i)}$), and
   the computer is further configured to learn the values of the number d of parameters ($\theta_1, \ldots, \theta_d$) on the basis of the number m of setpoint values ($\hat{Y}s_1^{(i)}, \ldots, \hat{y}s_m^{(i)}$) of the number m of first measured quantity values ($\hat{y}_1, \ldots, \hat{y}_m$) and the number m of training values ($\hat{y}t_1^{(i)}, \ldots, \hat{y}t_m^{(i)}$) of the number m of first measured quantity values ($\hat{y}_1, \ldots, \hat{y}_m$).

10. A measuring device for process metrology, comprising:
    a number of n sensors ($2_1$ to $2_n$), a respective sensor ($2_i$) of the number of o sensors being embodied to generate associated sensor data ($x_i$) such that a number of n sensor data ($x_1, \ldots, x_n$) is generated by way of the number of n sensors wherein
      the number of n sensors is selected from a group of sensors comprising at least one of:
        a radiometric sensor which is embodied to generate sensor data in the form of a count rate or radiation intensity data,
        a radiometric sensor which is embodied to generate sensor data in the for of information about radiometric spectra,
        an ultrasonic sensor or laser sensor which is embodied to generate sensor data in the form of information about a load height profile, or
        a microwave sensor;
    a computer to learn using a learning algorithm, values of a number d of parameters ($\theta_1, \ldots, \theta_d$) of a hypothesis function ($h_\theta$) based on training pairs (($xt_1^{(i)}, \ldots, xt_n^{(i)}$);($\hat{y}s_1^{(i)}, \ldots, \hat{y}s_m^{(i)}$));
    a processor communicatively coupled to the number of n sensors; and
    a memory in communication with the processor, the memory storing a plurality of instructions executable by the processor to cause the measuring device to:
      convert the number of n sensor data ($x_1, \ldots, x_n$) to a number m of first measured quantity values ($\hat{y}_1, \ldots, \hat{y}_m$) based on the hypothesis function ($h_\theta$) and the learned values of the number d of parameters ($\theta_1, \ldots, \theta_d$);
      convert the number of n sensor data ($x_1, \ldots, x_n$) to a number m' of second measured quantity values ($\tilde{y}_1, \ldots, \tilde{y}_{m'}$) depending via a model function (g);
      determine the validity of the first measured quantity values ($\hat{y}_1, \ldots, \hat{y}_m$) on the basis of the second measured quantity values ($\tilde{y}_1, \ldots, \tilde{y}_{m'}$), wherein the number m of first measured quantity values ($\hat{y}_1, \ldots, \hat{y}_m$) is selected from a group of measured quantity values comprising:
      measured quantity values of a fill level,
      measured quantity values of positions and/or thicknesses of individual material layers,
      measured quantity values of a density,
      measured quantity values of a conveying capacity, including an overall conveyed mass,
      measured quantity values of a throughput, including a mass flow,
      measured quantity values of a moisture,
      measured quantity values of a content of solid matter,
      measured quantity values of a sugar content,
      measured quantity values of a concentration, or
      a material composition, including chemical compositions.

11. A measuring device for process metrology, comprising:
    a number of n sensors ($2_1$ to $2_n$), a respective sensor ($2_i$) of the number of n sensors being embodied to generate associated sensor data ($x_i$) such that a number of n sensor data ($x_1, \ldots, x_n$) is generated by way of the number of n sensors;
    a computer to learn, using a learning algorithm values of a number d of parameters ($\theta_1, \ldots, \theta_d$) of a hypothesis function ($h_\theta$) based on training pairs (($xt_1^{(i)}, \ldots, xt_n^{(i)}$);($\hat{y}s_1^{(i)}, \ldots, \hat{y}s_m^{(i)}$));
    a processor communicatively coupled to the number of n sensors; and
    a memory in communication with the processor, the memory storing a plurality of instructions executable by the processor to cause the measuring device to:
      convert the number of n sensor data ($x_1, \ldots, x_n$) to a number m of first measured quantity values ($\hat{y}_1, \ldots, \hat{y}_m$) based on the hypothesis function ($h_\theta$) and the learned values of the number d of parameters ($\theta_1, \ldots, \theta_d$);
      convert the number of n sensor data ($x_1, \ldots, x_n$) to a number m' of second measured quantity values ($\tilde{y}_1, \ldots, \tilde{y}_{m'}$) depending via a model function (g);
      determine the validity of the first measured quantity values ($\hat{y}_1, \ldots, \hat{y}_m$) on the basis of the second measured quantity values ($\tilde{y}_1, \ldots, \tilde{y}_{m'}$), wherein the number n of n sensors is selected from a group of sensors comprising at least one of:
        a radiometric sensor which is embodied to generate sensor data in the form of a count rate or radiation intensity data,
        a radiometric sensor which is embodied to generate sensor data in the form of information about radiometric spectra,
        an ultrasonic sensor or laser sensor, which is embodied to generate sensor data in the form of information about a load height profile, or
        a microwave sensor.

* * * * *